United States Patent [19]
Huffman et al.

[11] Patent Number: 4,469,679
[45] Date of Patent: Sep. 4, 1984

[54] OCTAPEPTIDE VASOPRESSIN ANTAGONISTS

[75] Inventors: William F. Huffman, Malvern; Michael L. Moore, Media, both of Pa.

[73] Assignee: SmithKline Beckman Corporation, Philadelphia, Pa.

[21] Appl. No.: 467,117

[22] Filed: Feb. 16, 1983

[51] Int. Cl.$^3$ .................... A61K 37/00; C07C 103/52
[52] U.S. Cl. ............................. 424/177; 260/112.5 R
[58] Field of Search .................. 260/112.5 R; 424/177

[56] References Cited

U.S. PATENT DOCUMENTS 4,367,225 1/1983 Manning et al.
4,399,125 8/1983 Manning et al. ............. 260/112.5 R

FOREIGN PATENT DOCUMENTS 61356 of 0000 European Pat. Off.

OTHER PUBLICATIONS

M. Manning et al., J. Med. Chem. 25 414–419 (1982).
M. Manning et al., J. Med. Chem. 25 45–50 (1982).
T. Barth et al., Collection Czechoslov. Chem. Commun. 39, 506 (1974).
B. Berde et al., Handb. Exp. Pharm. 23 860 (1968).
D. B. Hope et al., J. Biol. Chem., 237 (1963).

Primary Examiner—Delbert R. Phillips
Attorney, Agent, or Firm—William H. Edgerton; Richard D. Foggio; Alan D. Lourie

[57] ABSTRACT

Certain octapeptides which have structures characterized by being a six unit cyclic peptide ring with a dipeptide tail have vasopressin antagonist activity. An important species of the group is [1-($\beta$-mercapto-$\beta$,$\beta$-cyclopentamethylenepropionic acid)-2-(O-ethyl-D-tyrosine)-4-valine-8-arginine-9-desglycine]vasopressin.

18 Claims, No Drawings

OCTAPEPTIDE VASOPRESSIN ANTAGONISTS

This invention relates to cyclic octapeptides which are vasopressin antagonists. More specifically, the structures of these octapeptides have 1-(β-mercapto-β,β-cyclopentamethylenepropionic acid) and five amino acid units cyclized into a 6-unit ring by means of a sulfur derived from a cysteine unit and a sulfur from the propionic acid unit, the ring further having a distinguishing dipeptide tail attached via an amido linkage to the cysteine unit.

BACKGROUND OF THE INVENTION

M. Manning, W. H. Sawyer and coworkers have published a series of papers describing various [1-β-mercapto-β,β-cyclopentamethylenepropionic acid), 4-valine]-arginine-vasopressin congeners which have anti-vasopressin activity. Among these are J. Med. Chem. 25 414–419 (1982), J. Med Chem. 25 45–50 (1982), EPA No. 61,356 and U.S. Pat. No. 4,367,225.

All of the Manning compounds have a tripeptide chain attached at unit 6 and are, of course, nonapeptides. The present compounds are distinguished over these by being octapeptides, having a dipeptide tail at unit 6 and by having potent vasopressin antagonist activity.

The potent biological activity of the compounds of the present invention is unexpected in view of the fact that de-glycinamide[9]-vasopressin and de-lysine[8]-glycinamide[9]-vasopressin [T. Barth et al., Collection Czechoslov. Chem. Commun. 39, 506 (1974)] as well as deGly[9]-oxytocin [B. Berde et al., Handb. Exp. Pharm. 23 860 (1968)] retain little of the activity of their respective parent compounds. It should be noted that "de" is used above to indicate the lack of the cited unit of the peptide, LVP or oxytocin, as in the cited publications. Hereafter, the term "des" is used for this purpose as is more common.

In the description herein and in the claims, the nomenclature common in the art of peptide and vasopressin chemistry is used. When no configuration is noted, the amino acid unit is in the L, or naturally occuring, form.

DESCRIPTION OF THE INVENTION

The compounds of the invention are illustrated by the following structural formula:

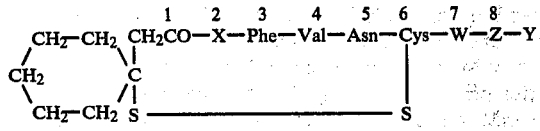

in which:
X is D-Phe, D-Val, D-Leu, D-Ile, D-norVal, D-Pba, D-norLeu, D-Cha, D-Abu, D-Met, D-Tyr or D-Tyr(alk);
Y is $NH_2$, NHalk, NHbzl or OH;
W is pro or ΔPr (dehydro-Pro);
Z is D-Arg, L-Arg, D-Lys or L-Lys, or a pharmaceutically acceptable salt thereof.

"Alk" represents a lower alkyl of 1–4 carbons which are optionally attached either to the nitrogen at Y or to the oxygen substituent of the tyrosine unit when present at position 2. Such alkyl substitutes include methyl, ethyl, n-propyl, isopropyl or butyl. "Bzl" represents benzyl. When the term, "vasopressin", is used, it means L-arginine vasopressin (AVP) unless otherwise modified. The AVP derivatives of this invention are preferred.

A subgeneric group of compounds of this invention comprises compounds of formula I in which X is D-Tyr, D-Cha, D-Phe, D-Ile, D-Leu, D-Val or D-Tyr(Et); Y is $NH_2$ or OH; W is Pro and Z is L-Arg.

Individual compounds of interest are [1-(β-mercapto-β,β-cyclopentamethylenepropionic acid)-2-D-tyrosine-4-valine-8-arginine-9-desglycine]vasopressin, [1-(β-mercapto-β,β-cyclopentamethylenepropionic acid)-2-D-tyrosine-4-valine-8-arginine-9-desglycinamide]-vasopressin and, especially, [1-(β-mercapto-β,β-cyclopentamethylenepropionic acid)-2-(O-ethyl-D-tyrosine)-4-valine-8-arginine-9-desglycine]vasopressin.

Also included in this invention are addition salts and complexes of the described compounds, especially the nontoxic, pharmaceutically acceptable salts. The acid addition salts are prepared in standard manner in a suitable solvent from the parent compound and an excess of an acid, such as hydrochloric, hydrobromic, sulfuric, phosphoric, acetic, maleic, succinic, ethanedisulfonic or methanesulfonic acids. Normally, the compounds of formula I in which Y is OH are used in the non-salt form.

The compounds of formula I are prepared by cyclizing a linear octapeptide by means of the two mercapto groups, respectively at the cysteine unit at position 6 and the β-mercapto-β,β-cyclopentamethylenepropionic acid unit (Pmp) at position 1. The cyclization reaction occurs in the presence of any mild oxidizing agent capable of oxidizing a mercaptan to a disulfide.

For example, oxidation of the following linear octapeptide;

in which X, W, Z and Y are as defined for formula I with the mercapto groups being members of the Pmp and Cys units, is carried out as described above. An excess of an alkali metal ferricyanide, such as potassium or sodium ferricyanide, is used with the linear intermediate dissolved in a suitable unreactive solvent, preferably in an aqueous solvent, at a neutral pH, about 7–7.5, at ambient temperature or lower until the reaction is substantially complete. Preferably, the concentrations of the linear peptide dimercaptan and the oxidizing agent are low, say 0.1 molar concentration of oxidizing agent in several liters of aqueous solution of cyclize 1–5 grams of dimercaptan.

Other mild oxidation agents having an oxidation potential roughly equivalent to ferricyanide may also be used for the ring closure reaction. Oxygen passage through the reaction solution for several days or iodine in methanol are alternatives. Cyclization, also, occurs when a thiol protective group such as that at the mercaptan group of the Pmp unit is displaced intramolecularly. Of course, one skilled in the art will recognize that certain cyclization methods are not appropriate if an interfering reaction site is present in the structure of the starting material of formula II. The linear mercaptan starting material may or may not have protective groups common to the art present at the various amino acid units.

The desired cyclic octapeptide of formula I is conveniently isolated by acidifying the aqueous oxidation mixture, such as using glacial acetic acid, and passing the reaction mixture over an ion-exchange chromatographic column, for example, over a weakly acid, acrylic resin column with acid elution, or by gel filtration over a bead-formed gel prepared by cross-linking dextran with epichlorohydrin.

The important intermediates of formula II are conveniently prepared using solid-phase methods of peptide synthesis as discussed in M. Manning et al., J. Med. Chem. 25 46 (1982). A commercial benzhydrylamine support resin (BHR) is used to prepare the end products of formula I in which Y is $NH_2$ (the des-glycines) and a chloromethyl support resin (CMR) is used to prepare the compounds of formula I in which Y is OH (the des-glycinamides).

The peptide chain of the linear peptides of formula II is built up, stepwise, proceeding from unit 8 working toward unit 1. Each unit is properly protected as known in the peptide art and as described below. The sequence of step reactions is conveniently carried out in a Beckman 990B peptide synthesizer without isolation of each intermediate peptide. The details of the procedure are in the working examples presented hereinafter.

The various amino acids, which are consecutively added to the resin supported chain are protected as known to the art. For example, the Boc protecting group is used for an amino group especially at the α-position; an optionally substituted benzyl, for the mercapto groups at the Pmp and Cys units; tosyl, for the Arg unit; and an optionally substituted carbobenzoxy(Z) for the Tyr or Lys units. The protective groups should, most conveniently, be those which are easily removed, that is, using acid treatment for the tert.-butyloxycarbonyl group, sodium-liquid ammonia or catalytic hydrogenation for the benzyl or carbobenzoxy groups. Other protective groups are known to the art, such as those reported in U.S. Pat. Nos. 4,322,340, 4,328,214 or 4,331,661 as well as in Protective Groups in Organic Chemistry, J. F. W. McOmie, Plenum, 1973.

The protected linear peptide intermediate is split from the carrying resin matrix, for example, by using ammonia in an aqueous miscible solvent, and, then, is treated to remove the protective groups, such as by using sodium-liquid ammonia. This procedure gives the amide derivative of the linear octapeptide.

More conveniently, the two steps are combined by treating the resin supported peptide with anhydrous hydrogen fluoride in a suitable organic solvent, such as anisole, to give the octapeptide intermediate of formula II in good yield.

The compounds of this invention have potent vasopressin antagonist activity. Vasopressin is known to contribute to the anti-diuretic mechanism of action within the kidney. When the action of these compounds antagonizes that of the natural anti-diuretic hormone (ADH), the body excretes water due to an increased permeability of the terminal portions of the renal tubule. We believe the mechanism of action is at the vasopressin receptors [$V_2$-receptors] located on the plasma membrane of certain renal epithelial cells. The most notable pharmocodynamic effect of the ADH antagonists of the invention is that of a water diuretic rather than of a natriuretic such as a thiazide.

Any patient suffering from the syndrome of inappropriate antidiuretic hormone secretion (SIADH) or from an undesirable edematous condition is a target for the claimed compounds. Examples of clinical conditions indicated for the compounds of this invention include hypertension, hepatic cirrhosis, congestive heart failure or a component of any traumatic condition resulting from serious injury or disease.

The second group of vasopressin receptor sites are the vascular pressor sites ($V_1$-receptors) within the cardiovascular system itself. These may also be somewhat antagonized by the compounds of this invention. Dysmenorrhea is another utility for the compounds of this invention when administered intravenously or intranasally.

The compounds of this invention, therefore, are used to treat edema or to expell water in patients in need of such treatment by administering parenterally or by insufflation a nontoxic but effective quantity of the chosen compound, preferably combined with a pharmaceutical carrier. Dosage units of the active ingredient are selected from the range 0.01 to 10 mg/kg, preferably 0.01 to 5 mg/kg, based on a 70 kg patient. The dosage units are applied from 1 to 5 times daily.

The pharmaceutical composition which contains an active ingredient of formula I comprises a dosage unit as described above dissolved or suspended in a standard liquid carrier, such as isotonic saline, contained in an ampoule or a multiple dose vial suitable for a parenteral injection such as for intravenous, subcutaneous or intramuscular administration. A composition for insufflation may be similar but is usually administered in a metered dose applicator or inhaler. Pulverized powder compositions may, also, be used along with oily preparations, gels, buffers for isotonic preparations, emulsions or aerosols.

In the disclosure of this invention, nomenclature common in the peptide art is used, see, for example, U.S. Pat. Nos. 4,358,440 (column 2) and 4,322,340 (columns 4 and 5) as well as the Manning publications referred to above. In this specific art, AVP refers to arginine vasopressin. It should be noted that the lysine vasopressin (LVP) antagonists are also claimed here. Pmp refers to $\beta$-mercapto-$\beta,\beta$-cyclopentamethylenepropionic acid which is the 1 position unit of the octapeptide structures of this invention.

The compounds of this invention have been demonstrated to have unique antagonistic activity toward the natural antidiuretic hormone (anti-ADH activity), in vitro, in the medullary tissue of hog kidney and, in vivo, in the hydropenic rat.

HOG KIDNEY ASSAY

A. Preparation of renal medullary membranes:

The medullary tissue of 24 kidneys of freshly slaughtered hogs is carefully dissected. The tissue is homogenized at 0° in a blender at maximal speed for one minute in 5 mM tris(hydroxymethyl)aminomethane (TRIS) buffer pH 8.0 containing 3.0 mM magnesium chloride, 1.0 mM ethylenediaminetetraacetic acid and 0.25 M sucrose (TRIS-sucrose buffer used at 10 ml of buffer per gram of tissue.) The tissue is homogenized in a Potter-Elvehjem homogenizer equipped with a Teflon pestle. The homogenate is passed through one layer of cheesecloth with one volume of TRIS-sucrose buffer. The 300 times gravity supernatant is centrifuged at 1200 times gravity. The resulting pellet is washed with 5 mM TRIS buffer at pH 8 containing 3.0 mM magnesium chloride and 1 mM ethylenediaminetetracarboxylic acid (hypotonic Tris buffer; 6×10 ml of buffer per gram of tissue). The washed pellet is suspended in hypotonic TRIS buffer (1.0 ml per gram of tissue) and stored in aliquots in liquid nitrogen.

B. Assay of Adenylate Cyclase Activity:

The incubation mixture contains 100 mM TRIS, 0.1% bovine serum albumin (BSA), 10 mM magnesium chloride, 1 mM c-adenosine monophosphate, 0.25 mM adenosine triphosphate, 0.6–1.2 μCi [α-$^{32}$P]-adenosine triphosphate (specific activity in 30 Ci/mmol), 20 mM creatine phosphate, 1 mg creatine kinase/ml, 1 mM ethyleneglycolbis-(β-aminoethylether)-N,N'-tetraacetic acid, renal medullary membranes (0.5–1.0 mg/ml), vasopressin and the test compound. The total volume is 300 μl; the pH is 8.0 at 30° C. The mixture is incubated for 20 minutes at 30°, the tubes are transferred to ice water, 100 μl of a stopping solution (1% sodium lauryl sulfate containing 10 mM cyclic-adenosine monophosphate, $^3$H cyclicadenosine monophosphate 1500 dpm/100 μl and 45 mM ATP; the pH was adjusted to 8.0 at 25° with 2 M TRIS) is added followed by 500 μl of ice cold water. The $^{32}$P/cAMP formed was isolated by chromatography on aluminum oxide and "Dowex" AG 50W-X8. $^3$H cAMP serves as control.

C. Test Procedure for Assay of Adenylate Cyclase Activity:

In each experiment the amount of $^{32}$P/cAMP formed in the absence of medullary membrane is determined (blank). The blank value is substracted from all experimental data. The compound is tested for its effect on basal adenylate cyclase activity and/or on vasopressin stimulated activity. Each determination is carried out in triplicate. The Ka value is derived from a Lineweaver-Burke plot. Rel. $V_{max} = (V_{max}\text{drug}/V_{max} \text{ vasopressin}) \times 100$. $K_i = I/[(Ka'/Ka)-1]$ where I is the concentration of the antagonist, and Ka' and Ka are the concentrations of vasopressin required to give half-maximal activity of adenylate cyclase in the presence and absence of antagonist, respectively.

D. Inhibition of Vasopressin Binding:

The incubation mixture contains 100 mM Tris, 0.5% BSA, 10 mM magnesium chloride, 1 mM cAMP, 0.25 mM ATP, $^3$H-vasopressin, test compound and membranes (0.5–1.0 mg protein/ml). The total volume is 100 μl; the pH is 8.0 at 30°. After incubating for 20 minutes at 30°, 2 ml of ice-cold 100 mM Tris:HCl buffer pH 8.1 (at 5°) containing 1.0 mM magnesium chloride, 1 mM cAMP, and 0.25 mM ATP are added and the mixture is immediately filtered through prewashed Millipore filters (the filters are prewashed with 5 ml of ice-cold 10 mM Tris:HCl buffer pH 8.1 at 5°—containing 0.1% BSA and 1 mM MgCl$_2$—Solution A). The filters are rapidly washed with 4×5 ml ice-cold solution A.

E. Test Procedure for Binding Assay:

In each experiment, the amount of $^3$H-vasopressin bound in the absence and in the presence of an excess of vasopressin (7.5×10$^{-6}$ M) is measured in triplicate. These values represent total and non-specific binding, respectively. The $K_B$ of a compound is derived from the equation for competitive inhibition: $K_B = IC_{50}/(1+L/K_D)$, where $IC_{50}$ is the concentration required for 50% inhibition of $^3$H-vasopressin binding, L is the concentration of the ligand, and $K_D$ is the dissociation constant of $^3$H-vasopressin ($K_D=3.6\times10^{-9}$ M; 1 SD=0.4×10$^{-9}$ M). This is the average $K_D$ value determined on 3 preparations of hog kidney membranes.

HYDROPENIC RAT SCREEN

A. Food and water are removed from male rats approximately 18 hours prior to testing. Animals are housed 4 per metabolism cage. At 0 hour, the test compound is administered intraperitoneally to the test group and an equivalent volume of vehicle is administered to both control groups (fasted and non-fasted). Urine volume and osmolality are measured every hour for 4 hours. Test values are recorded as ml of urine excreted (cumulative), mEq/rat electrolyte excreted, mg/rat urea excreted, and osmolality in milli-Osmoles/kg H$_2$O. A tolerance test is used to determine significance. ED$_{300}$ is defined as the dose of compound (μg/kg) required to lower urine osmolality to 300 m-Osmoles/kg. ED$_{500}$ is defined as the dose of compound (μg/kg) required to lower urine osmolality to 500 m-Osmoles/kg.

TABLE I

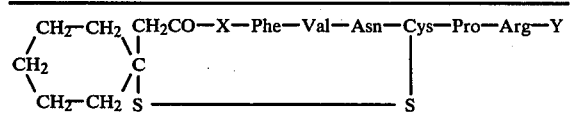

| compound | | anti-ADH activity | | |
|---|---|---|---|---|
| | | in vivo (Rat) | in vitro (Pig) | |
| X | Y | ED$_{300}$ (μg/kg)* | Ki(nM) | K$_B$ (μM) |
| 1. D-Tyr | Gly—NH$_2$ | 32 | 30 | 0.10 |
| 2. D-Tyr | NH$_2$ | 63 | 28 | 0.039 |
| 3. D-Tyr | OH | 156 | 190 | 0.24 |
| 4. D-Tyr(Et) | Gly—NH$_2$ | 6.5 | 6.0 | 0.010 |
| 5. D-Tyr(Et) | NH$_2$ | 5.0 | 13 | 0.016 |

*Estimated dose of peptide delivered ip stat (μg/kg) which results in a reduction of U$_{osm}$ from hydropenic levels to 300 m-Osmoles/kg H$_2$O.

The table of biological test results presented above demonstrates that three representative compounds (2, 4 and 5 of Table I), whose octapeptide structures have the dipeptide tail characteristic of the compounds of this invention, have anti-ADH activity of the same order as do certain nonapeptides (1 and 3) whose structures have a tripeptide tail. This result is unexpected because the de-Gly-oxytocin has the opposite effect on blood pressure compared with oxytocin itself (See B. Berde et al., loc. cit.) and shortening the linear tail of oxytocin and vasopressin results in "a striking decrease of the typical biological activities of the substances" (see T. Barth et al., loc. cit.). Compound 5 of Table I, furthermore, has proven to be a compound of exceptional antagonist activity compared with the prior art compounds or with other members of the genus of this invention.

The following examples are intended solely to teach the preparation of the compounds of this invention. All temperatures are in degrees Centigrade.

EXAMPLE 1

Solid-Phase Synthesis of Pmp(Bzl)-D-Tyr(Br-Z)-Phe-Val-Asn-Cys(OMe-Bzl)-Pro-Arg(Tos)-Resin For the solid-phase synthesis of the titled resin supported peptide, Boc-Arg(Tos)-resin (3 mM/5.4 grams of resin) was used as starting material. The appropriately protected amino acids were coupled sequentially onto the Boc-Arg(Tos)-resin, prepared by reacting Boc-Arg(Tos) as the cesium salt with commercial Merrifield resin (Cl-CH$_2$-resin) as known to the art, by using a manual program as described in the following steps:

1. washed with methylene chloride (3 times, 1 minute).
2. prewashed with 33% trifluoroacetic acid in methylene-chloride with 1% indole (1 time, 1 minute).
3. deprotection with 33% trifluoroacetic acid in methylene-chloride with 1% indole (20 minutes).

4. washed with methylene chloride (1 time, 1 minute).
5. washed with ethanol (1 time, 1 minute).
6. washed with methylene chloride (2 times, 1 minute).
7. prewashed with 10% triethylamine in methylene chloride (1 time, 1 minute).
8. neutralization with 10% triethylamine in methylene chloride (10 minutes).
9. Protected amino acid (10 mM) in triethylamine in methylene chloride and 0.5 M N,N'-dicyclohexylcarbodiimide in methylene chloride (20 ml) were added and the reaction time was up to two hours.

In the case of the coupling of the Asn moiety, 1-hydroxybenzotriazole (HBT, 10 mM) was added with Boc-Asn in dry dimethylformamide. Dry dimethylformamide (DMF) was also used as solvent when Pmp(Bzl) was coupled onto the peptide resin, using 4-dimethylaminopyridine (10 mM). Completion of each coupling reaction was monitored by the ninhydrin test. The p-methoxybenzyl group was used to protect the thiol group of Cys and the 2-bromo-carbobenzoxy group was employed to block the phenolic hydroxyl of D-Tyr.

The resulting protected Pmp(Bzl)-D-Tyr(Br-Z)-Phe-Val-Asn-Cys(OMe-Bzl)-Pro-Arg(Tos)-resin was washed well with 33% trifluoroacetic acid in methylene chloride, methylene chloride and methanol, respectively. After drying in vacuo overnight, 8.4 grams of the titled protected resin intermediate was collected.

Preparation of

Pmp—D-Tyr—Phe—Val—Asn—Cys—Pro—Arg—NH2

Pmp(Bzl)-D-Tyr-(p-bromocarbobenzoxy)-Phe-Val-Asn-Cys(Ome-Bzl)-Pro-Arg(Tos)-Resin (4 g, ca. 1.5 mM) was subjected to ammonolysis using saturated ammonia/methanol solution (200 ml) in dry dimethylformamide (50 ml) at room temperature for 48 hours. After evaporation to dryness, the residue was precipitated by ethyl acetate/n-hexane and filtered to give the protected octapeptide amide (1.54 g).

This crude peptide was dissolved in liquid ammonia (250 ml) and treated with sodium/liquid ammonia solution to give Pmp-D-Tyr-Phe-Val-Asn-Cys-Pro-Arg-NH2 which was, then, oxidized using 0.01 M potassium ferricyanide solution in 4 l. of aqueous solution at pH 7-7.5. After the completion of oxidation reaction, the pH of aqueous solution was adjusted to pH 4.5 by adding glacial acetic acid. This solution was passed through a weakly acid acrylic resin (Bio-Rex 70) column (11×2.5 cm) slowly. The column was eluted with 5% and 50% acetic acid solution, respectively. Crude cyclized Pmp-D-Tyr-Phe-Val-Asn-Cys-Pro-Arg-NH2 was collected from 50% acetic acid solution fractions (860 mg).

Purification of

Pmp—D-Tyr—Phe—Val—Asn—Cys—Pro—Arg—NH2

1. Counter-current distribution:
Sample: 860 mg crude, n-BuOH:HOAc:H2O 4;1;5; 250 transfers -continued

| | |
|---|---|
| (a) fr. 186-204, | 436 mg. |
| (b) fr. 182-185 & 205-218, | 219 mg. |

2. Partition chromatography:
Sample: 250 mg (from 1-a), G-25 fine (2.5 × 55 cm), n-BuOH:HOAc:H2O 4:1:5
  (a) fr. 32-46                       222 mg 3. Preparative HPLC:
Sample: 40 mg (from 2-a); Alltech C18, 3000 psig. Flow rate: 3.0 ml/min.
    Buffer A: 0.1% TFA
    Buffer B: 0.25% TFA:CH3CN 4:6
    60% B; isocratic; 235 nm (2.0 AUFS)
    Injection: 10 mg/0.5 ml. buffer A
17 mg pure sample.

4. Ion-exchange Chromatography:
Sample: 365 mg (from 1-a & 2-a); CMC; 0.01 M NH4OAc to 0.1 M NH4OAc

| | Linear gradient |
|---|---|
| (a) fr. 51-70 | 33.5 mg |
| (b) fr. 71-89 | 16.5 mg |
| (c) fr. 91-110 | 5 mg |
| (d) fr. 111-121 | 24.5 mg |

EXAMPLE 2

Preparation of

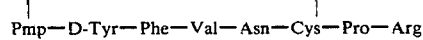

Pmp—D-Tyr—Phe—Val—Asn—Cys—Pro—Arg

Pmp(Bzl)-D-Tyr(Br-Z)-Phe-Val-Asn-Cys(OMe-Bzl)-Pro-Arg(Tos)-Resin (4.2 g, 1.5 mM) from Example 1, in 4.5 ml distilled amisole, was reacted with anhydrous hydrogen fluoride (40 ml) at 0° for one hour. After evaporation in vacuo to dryness, the residue was treated with anhydrous ether and filtered off to give 1.33 g crude peptide. The completion of removal of the Bzl group from the Pmp moiety was carried out using the sodium in liquid ammonia reaction as described in Example 1. The resulting unprotected octapeptide was cyclized using 0.01 M potassium ferricyanide solution at pH 7-7.5 until color persisted for 30 minutes again as described above in the preparation of the amide.

Desglycinamide octapeptide (600 mg) was collected after acidifying the oxidation solution with acetic acid to pH 4.5 and passing the reaction mixture over a Bio-Rex-70 column with 1 l. of 5% acetic acid as eluent.

Purification of

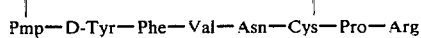

Pmp—D-Tyr—Phe—Val—Asn—Cys—Pro—Arg

1. Counter-current distribution:
Sample: 600 mg from Bio-rex 70. n-BuOH:HOAc:H2O 4:1:5; 200 transfers
  (a) fr. 150-161                   169 mg
  (b) fr. 133-149 & 162-163

2. Preparative HPLC:
Sample: 52 mg (from 1-a); Alltech C18 (25 cms 10 mm, 10 micron);
    Buffer A: 0.1% TFA
    Buffer B: 0.25% TFA:CH3CN 4:6
    60% B, isocratic; 3000 psig; 3.0 ml/min.
    Injection: 10 mg/0.6 ml in buffer A
    235 nm (2.0 AUFS).
  (a) 24 mg
  (b) 7.3 mg
Combine 2-a and 2-b, purified on HPLC to give 15 mg pure peptide.

3. Partition Chromatography

-continued

Sample: 117 mg (from 1-A), G-25 fine (2.5 × 55 cm)
n-BuOH:HOAc:H₂O 4:1;5
  (a) fr. 32-36                             83 mg

EXAMPLE 3

Preparation of

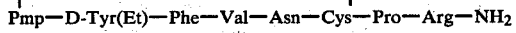
Pmp—D-Tyr(Et)—Phe—Val—Asn—Cys—Pro—Arg—NH₂

The titled compound was prepared by the solid phase method on benzhydrylamine resin (BHA). Thus, 1.0 g BHA resin (1.13 mmol NH₂/g resin) was reacted with 1.5 equivalents of Boc-Arg(Tos), 1.5 equivalents of DCC and 3.0 equivalents of HBT which were made up in dimethylformamide to be 0.1 M in Boc-Arg(Tos). Deblocking was performed with 50% TFA/methylene chloride and neutralization with 5% DIEA/methylene chloride. The peptide was elongated, stepwise, by coupling, using preformed Boc aminoacyl symmetrical anhydrides in DMF (0.1 M). Boc-Asn, Boc-D-Tyr(Et) and Pmp(MBz) were coupled with DCC and HBT in DMF. Completeness of coupling was monitored by the qualitative ninhydrin test and recoupling was performed as necessary. The completed Pmp(MBz)-D-Tyr-(Et)-Phe-Val-Asn-Cys(MBz)-Pro-Arg(Tos)-BHA resin was washed with methylene chloride and dried to constant weight, 2.34 g.

The peptide was deblocked and cleaved from the resin by treatment with anhydrous liquid hydrogen fluoride (30 ml) in the presence of anisole (4 ml) at 0° for one hour. After evaporation to dryness under vacuum, the resin was washed with ethyl ether, air dried and, then, extracted with degassed dimethylformamide (3×20 ml) and 20% acetic acid (4×20 ml). The DMF and acid extracts were added to 4 l of water (pH 4.5 with acetic acid). The pH was adjusted to 7.2 with ammonium hydroxide and the solution was titrated with 0.01 M potassium ferricyanide under argon with stirring until a yellow color persisted (85 ml). The pH was brought to 4.8 with glacial acetic acid. The mixture was filtered and the filtrate passed over a Bio-Rex 70 column (H⊕). After washing the column with water (200 ml) the crude peptide was eluted with 300 ml of pyridine:acetic acid:water (30:4:66 v/v). The eluant was evaporated under vacuum at 30°. The residue was dissolved in 100 ml of 0.2 N acetic acid, then, lyophilized, yielding 507 mg of the crude titled octapeptide.

Purification of

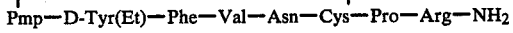
Pmp—D-Tyr(Et)—Phe—Val—Asn—Cys—Pro—Arg—NH₂

1. Counter-current distribution:
Sample: 607 mg crude, n-BuOH:HOAc:H₂O 4:1:5, 240 transfers
  (a) fr. 154-170 & 190-192                 71 mg
  (b) fr. 171-189                          230 mg
2. Gel filtration
Sample: 123 mg of Ib, G-15 (2.5 × 55 cm) 0.2 N HOAc, 25 ml/hr
  (a) fr. 46-50                            ~20 mg -continued (b) fr. 51-77                             60 mg pure peptide

EXAMPLE 4

Preparation of

Pmp—D-Leu—Phe—Val—Asn—Cys—Pro—Arg—NHC₃H₇

A mixture of 0.1 mmole of (Pmp¹-D-Leu²-Val⁴-desGlyNH₂⁹)VAP, prepared as described above using Boc-D-Leu at position 2, and 0.1 mmole of n-propylamine in 20 ml of DMF was reacted with 23 mg (0.11 mmole) of DCC and 14 mg (0.11 mmole) of HBT at room temperature for 2 hours. The volatiles were evaporated to give an oily product residue. The product was purified as described above using (1) gel filtration over G-10-Sephadex eluted with 0.2 N acetic acid, (2) high pressure liquid chromatography using 0.05% TFA in 39% acetonitrile in water and, again, (3) gel filtration to give 20 mg of the pure octapeptide of the title.

Amino acid analysis: Asp 0.88, Pro 0.93, Val 1.00, Leu 1.09, Phe 0.88, Arg 1.07. HPLC=95% major peak at 11.33 with 40% aqueous acetonitrile with 0.05 M KH₂PO₄ as buffer. K$_{bind}$=12.1% inhibition at 10⁻⁵ M.

Using (Pmp¹-D-Tyr(Et)²-Val⁴-desGlyNH₂⁹)AVP prepared as in Example 2 above and benzylamine gives

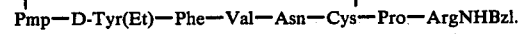
Pmp—D-Tyr(Et)—Phe—Val—Asn—Cys—Pro—ArgNHBzl.

Other N-alkylated derivatives are prepared similarly.

EXAMPLE 5

Substituting a stoichiometric quantity of Boc-D-Phe for Boc-D-Tyr(Br-Z) at the 2 unit of the peptide synthesis of Example 1 gives

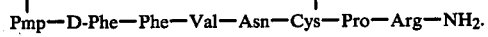
Pmp—D-Phe—Phe—Val—Asn—Cys—Pro—Arg—NH₂.

Substituting Boc-D-Val at the same position using the splitting-oxidation reactions of Example 2 gives

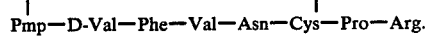
Pmp—D-Val—Phe—Val—Asn—Cys—Pro—Arg.

Substituting Boc-D-Leu in Example 1 gives

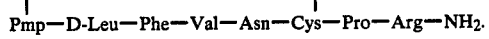
Pmp—D-Leu—Phe—Val—Asn—Cys—Pro—Arg—NH₂.

Substituting in Example 1 Boc-D-norLeu at the 2 unit and D-Arg(Tos) at the 8 unit gives

Pmp—D-norLeu—Phe—Val—Asn—Cys—Pro—D-Arg—NH₂.

Substituting in Example 2 Boc-D-Cha at the 2 unit gives

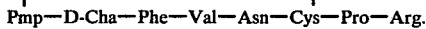

Substituting in Example 1 Boc-α-aminophenylbutyric acid (Pba) at the 2 unit gives

Substituting Boc-Lys(ClZ) in Example 3 for the protected Arg gives

Other representative compounds prepared in like manner are:

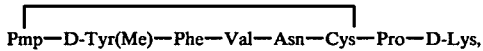

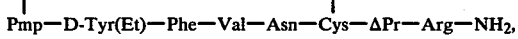

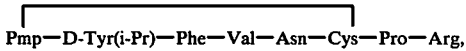

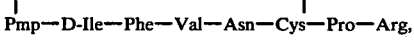

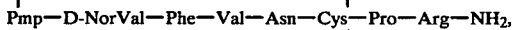

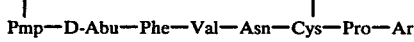

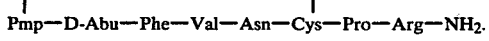

EXAMPLE 6

Parenteral Dosage Unit Compositions:

A preparation which contains 0.5 mg of the cyclic octapeptide of Examples 1 or 3 as a sterile dry powder for parenteral injection is prepared as follows: 0.5 mg of peptide amide is dissolved in 1 ml of an aqueous solution of 20 mg of mannitol. The solution is filtered under sterile conditions into a 2 ml ampoule and lyophylized. The powder is reconstituted before either intramuscular or intravenous injection to a subject suffering from edema susceptible to anti-ADH mechanism of action. The injection is repeated as necessary, from 1–5 times daily or in continuous i.v. drug injection. Other octapeptides of this invention are made up and used in like manner.

Nasal Dosage unit Compositions:

30 Mg of finely ground octapeptide of this invention such as the product of Example 2 is suspended in a mixture of 75 mg of benzyl alcohol and 1.395 g of a suspending agent such as a commercial mixture of semi-synthetic glycerides of higher fatty acids. The suspension is placed in an aerosol 10 ml container which is closed with a metering valve and charged with aerosol propellants. The contents comprise 100 unit doses which are administered intranasally to an edematous subject from 1–6 times a day.

What is claimed is:

1. A polypeptide having the formula:

$$\begin{array}{c} \phantom{xx} 1 \phantom{x} 2 \phantom{x} 3 \phantom{x} 4 \phantom{x} 5 \phantom{x} 6 \phantom{x} 7 \phantom{x} 8 \\ CH_2-CH_2 \phantom{x} CH_2CO-X-Phe-Val-Asn-Cys-W-Z-Y \\ /\phantom{xxxx}\backslash\,| \\ CH_2 \phantom{xxxxxx} C \\ \backslash\phantom{xxxx}/\,| \\ CH_2-CH_2 \phantom{x} S \phantom{xxxxxxxxxxxxxxxx} S \end{array}$$

in which:

X is D-Phe, D-Val, D-Leu, D-Ile, D-norVal, D-Pba, D-norLeu, D-Cha, D-Abu, D-Met, D-Tyr or D-Tyr(alk);

Y is NH$_2$, NHalk, NHbzl or OH;

W is Pro or dehydro-Pro; and

Z is D-Arg, L-Arg, D-Lys or L-Lys, alk being lower alkyl of 1–4 carbons, or a pharmaceutically acceptable salt thereof.

2. The compound of claim 1 in which X is D-Tyr or D-Tyr(alk), W is Pro, and Z is L-Arg.

3. The compound of claim 1 having the formula:

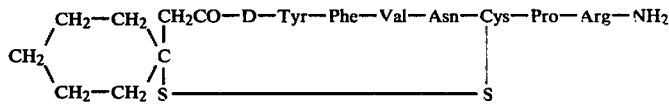

4. The compound of claim 1 having the formula:

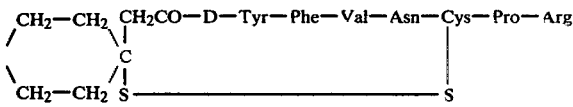

5. The compound of claim 1 having the formula:

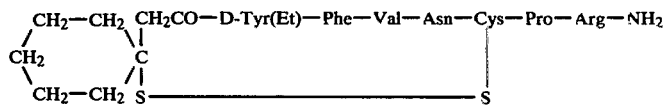

6. A pharmaceutical composition comprising a pharmaceutical carrier and, dispersed therein, a water diuretically effective but nontoxic quantity of a compound having the formula:

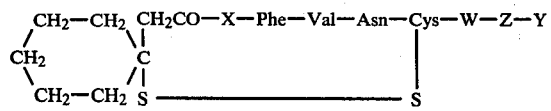

in which:

X is D-Phe, D-Val, D-Leu, D-Ile, D-norVal, D-Pba, D-norLeu, D-Cha, D-Abu, D-Met, D-Tyr or D-Tyr(alk);
Y is NH₂, NHalk, NHbzl or OH;
W is Pro or dehydro-Pro; and
Z is D-Arg, L-Arg, D-Lys or L-Lys,
alk being lower alkyl of 1–4 carbons, or a pharmaceutically acceptable salt thereof.

7. The composition of claim 6 in which the compound has the formula of claim 6 in which X is D-Tyr or D-Tyr(alk), W is Pro, and Z is L-Arg.

8. The composition of claim 6 in which the compound has the formula:

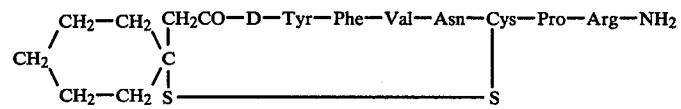

9. The composition of claim 6 in which the compound has the formula:

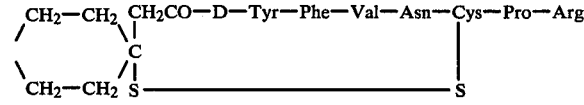

10. The composition of claim 6 in which the compound has the formula:

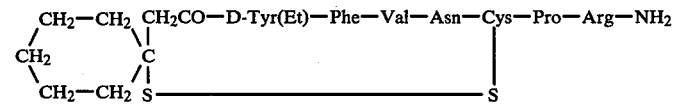

11. The composition of claim 6 in which the quantity of compound is selected from the range of 0.01–10 mg/kg.

12. The method of inducing a water diuretic effect in a patient in need of such an effect comprising administering parenterally or intranasally to said patient a nontoxic, effective quantity therefor of a compound of claim 1.

13. A method of claim 12 in which the compound has the formula:

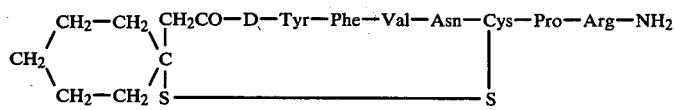

14. The method of claim 12 in which the compound has the formula:

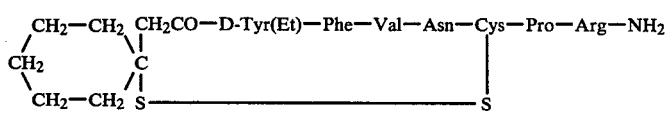

15. The method of claim 12 in which the quantity is selected from the range of 0.01–10 mg/kg administered from 1–5 times daily.

16. A polypeptide of the formula:

Pmp-X-Phe-Val-Asn-Cys-W-Z-Y in which:

X is D-Phe, D-Val, D-Leu, D-Ile, D-norVal, D-Pha, D-norLeu, D-Cha, D-Abu, D-Met, D-Tyr or D-Tyr(alk);
Y is NH₂, NHalk, NHbzl or OH;
W is Pro or dehydro-Pro; and
Z is D-Arg, L-Arg, D-Lys or L-Lys, alk being lower alkyl of 1–4 carbons, or a pharmaceutically acceptable salt thereof.

17. The compound of claim 16 being Pmp-D-Tyr-Phe-Val-Asn-Cys-Pro-Arg-NH₂.

18. The compound of claim 16 being Pmp-D-Tyr(Et)-Phe-Val-Asn-Cys-Pro-Arg-NH₂.

* * * * *